United States Patent [19]

Westerkamp et al.

[11] Patent Number: 4,928,683

[45] Date of Patent: May 29, 1990

[54] RESPIRATING APPARATUS FOR PATIENTS

[76] Inventors: Bart Westerkamp; Geert Van Dijk, both of Pampuslaan 90, Weesp, Netherlands

[21] Appl. No.: 151,675

[22] Filed: Feb. 2, 1988

[30] Foreign Application Priority Data

Feb. 17, 1987 [NL] Netherlands ............. 8700389

[51] Int. Cl.⁵ ............................................. A61M 15/00
[52] U.S. Cl. ..................... 128/203.12; 128/203.14; 128/204.18; 128/204.21; 128/205.12
[58] Field of Search ............... 128/204.18, 204.21, 128/203.12, 203.14, 204.22, 205.12, 205.16; 417/339, 393, 395

[56] References Cited

U.S. PATENT DOCUMENTS

| | | | |
|---|---|---|---|
| 2,673,525 | 3/1954 | Lucas | 417/395 |
| 3,200,816 | 8/1965 | Bartlett, Jr. | 128/204.21 |
| 3,213,804 | 10/1965 | Sobey | 417/395 |
| 3,270,672 | 9/1966 | Haines et al. | 417/339 |
| 3,338,171 | 8/1967 | Conklin et al. | 417/339 |
| 3,599,633 | 8/1971 | Beasley | 128/204.18 |
| 3,630,642 | 12/1971 | Osterman | 417/393 |
| 3,754,550 | 8/1973 | Kipling | 128/205.16 |
| 3,864,060 | 2/1975 | Hall, Jr. et al. | 417/395 |
| 4,037,616 | 7/1977 | Pinkerton | 417/393 |
| 4,468,177 | 8/1924 | Strimling | 128/1 D |
| 4,634,430 | 1/1987 | Polaschegg | 417/395 |

FOREIGN PATENT DOCUMENTS

| | | | |
|---|---|---|---|
| 0121255 | 10/1984 | European Pat. Off. | 128/203.12 |
| 1273586 | 9/1961 | France | 417/339 |

Primary Examiner—Edgar S. Burr
Assistant Examiner—Aaron J. Lewis
Attorney, Agent, or Firm—Pollock, VandeSande and Priddy

[57] ABSTRACT

Respirating apparatus comprising a pump, by means of which respiratory gas may be circulated in a closed line system in which the pressure may be varied in accordance with a certain respirating pattern, said line system being provided with connecting means for a patient and for supplying the various components of the respiratory gas and with means for withdrawing the carbon dioxide exhaled by the patient into the line system, said pump including at least one pump chamber which is separated by a pump membrane into a primary and a secondary portion, in which the secondary portion forms part of or is connected to the line system and the primary portion is connected to a supply of a driving fluid, of which the varying pressure may effect the pumping action of the membrane.

5 Claims, 1 Drawing Sheet

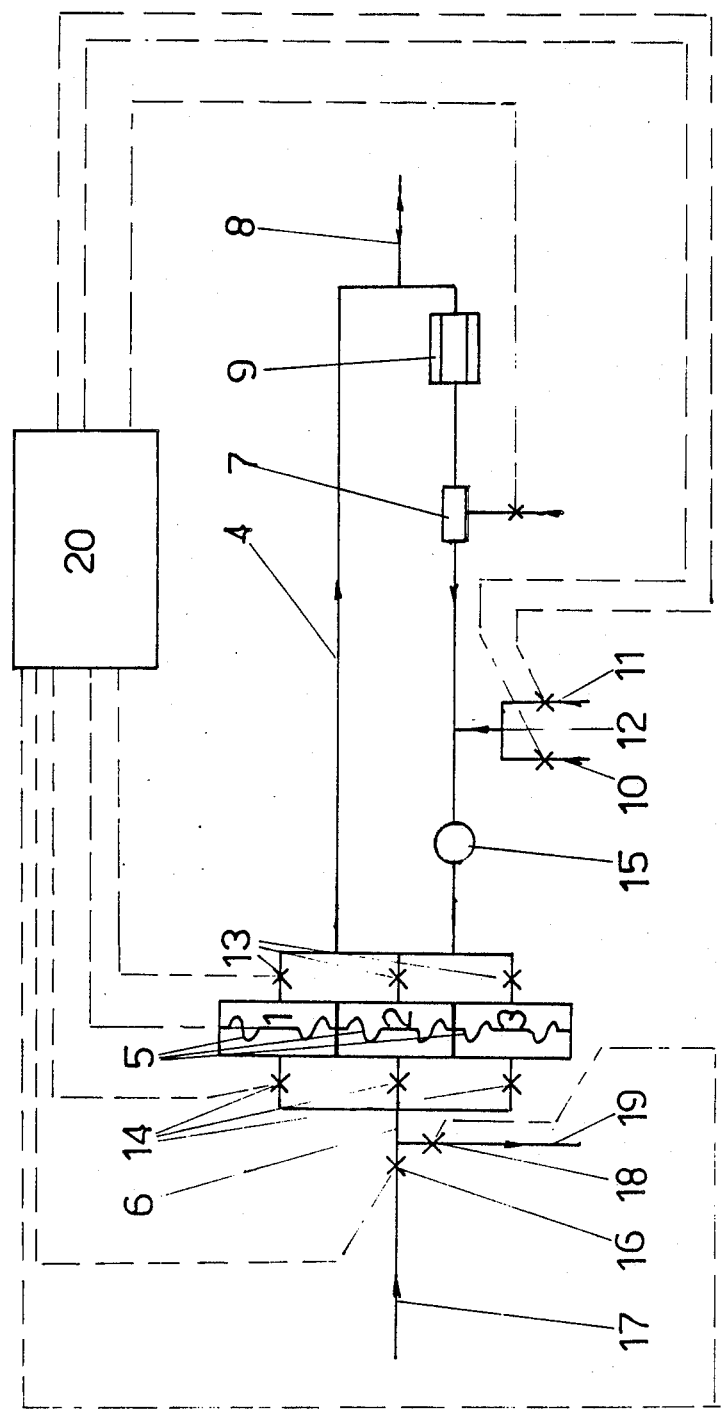

RESPIRATING APPARATUS FOR PATIENTS

The present invention relates to a respiration apparatus for patients, more particularly for anesthesia, which apparatus is provided with a pump, by means of which respiratory gas may be circulated in a closed line or conduit system and the pressure in this line system may be varied in accordance with a certain respirating pattern, the line system being provided with connecting means for the patient and with further connecting means for supplying the various components of the respiratory gas and with means for withdrawing carbon dioxide exhaled by the patient into the line system.

Such an apparatus is known. The known apparatus comprises a pump connected on its downstream side to a volume displacement meter formed as a single cylinder, in which a clock shaped piston may be moved backwards and forwards over an intermediate mounted roller membrane. This known construction has the disadvantage of being complicated, and in addition the discharge of the pump and the control of the pressure in the line system can not be performed with great accuracy.

It is an object of the invention to obviate this disadvantage of the known apparatus.

The apparatus according to the invention thereto is characterized in that the pump includes at least one pump chamber, which is separated by a pump membrane into a primary and a secondary portion, in which the secundary portion forms part of or is connected to the line system and the primary portion is connected to a supply of a driving fluid, of which the varying pressure may effect the pumping action of the membrane.

As opposed to the known apparatus, in the apparatus according to the invention the pump also performs the function of a volume displacement meter.

The driving fluid may be of different form such as for instance and preferably in the form of compressed air.

According to a next feature of the apparatus according to the invention, the pump comprises several pump chambers connected in parallel. In this embodiment of the apparatus according to the invention, the supply and/or the discharge of the primary, respectively the secondary portions of the pump chambers are provided with closing devices, by means of which one or more pump chambers may be brought into or out of operation.

By applying more pump chambers connected in parallel and which seperately may be brought into and out of operation, a more accurate control or regulation of the respiration of the patient has become possible.

In a favorable embodiment of the apparatus according to the invention, means are present for determining the membrane displacement and the volume change connected thereto of the secondary portion of a pump chamber.

These means may be differently shaped.

In a favorable embodiment of the apparatus according to the invention, the means may act in a capacitive or inductive manner.

In operation and by the pressure variation of the driving fluid in the primary portion of the pump chamber, the membrane is brought into a reciprocal movement and by which a certain pumping action is achieved.

According to a further feature of the apparatus according to the invention, the movement of the membrane towards the secondary portion of the pumping chamber is favorably limited in an end position by a stop member present within the primary portion of the pumping chamber.

In a preferred embodiment of the invented apparatus, the membrane of a pumping chamber may be moved to an end position against the action of a spring. In a further working out of this embodiment of the apparatus according to the invention, the spring force, against which the succeeding membranes of the pump chambers connected in parallel may be moved to the end positions, increase gradually, such that, by increasing the pressure of the driving fluid, at first the membrane with the smallest opposing spring force is moved from the initial position wholly to the end position, then the next membrane is moved by the driving fluid from the initial position to the end position, and so on.

In this embodiment of the apparatus according to the invention the discharge of the pump may be accurately controlled in a simple and efficient way by controlling the pressure of the driving fluid at the primary side of the membranes.

In a further working out of the invented apparatus, the line system comprises a non-positive-displacement pump, such as a centrifugal pump, and by means of which the respiratory gas may be circulated in the line or conduit system.

By applying such a special circulation pump in the line system, the same may be carried out completely free from check valves, on account of which the sensitiveness of the apparatus for disturbances is considerably reduced.

Further, by applying a special circulation pump, a liquid anestheticum may be supplied in a favorable way directly into the line system to be evaporated in the gas flow.

An embodiment of the invention will now be described by way of example only with reference to the accompanying drawing.

As is shown in the drawing, the apparatus is provided with a membrane pump being three pump chambers 1, 2 and 3, connected in parallel, and by means of which the respiratory gas in a closed conduit system 4 may be alternately compressed according to a certain respiratory pattern.

Each of the pump chambers 1, 2 and 3 is divided by a membrane 5 into a primary portion, which is connected to a supply/discharge line 6 for compressed air that is used as the driving fluid, and a secondary portion, which is connected to the closed line system 4.

The line system 4 further is provided with connecting means 8 for the patient, with an absorbing device 9 to withdraw the carbon dioxide exhaled by the patient into the line system, with connections 10, 11 and 12 for introducing into the line system laughing gas (N O) and oxygen, and with a evaporator with a supply 7 for liquid anesthetica.

The secondary portions of the pump chambers 1, 2 and 3 are connected to the line system 4 via valves 13, while the primary portions of the pump chambers 1, 2 and 3 are connected via valves 14 to the supply/discharge line 6 for the compressed air.

The line system further comprises a circulation pump 15 to circulate and to mix the components of the respiratory gas in the line system 4.

The supply/discharge line 6 of the compressed air is connected via an electro-magnetically operable valve 16 and a control valve, which is not shown in the drawing, to a compressed air supply 17, and via an electromagnetically operable valve 18 to a compressed air discharge or blow off line 19.

The secondary portions of the pump chambers 1,2 and 3 are provided with measuring device (not shown in the drawing), by means of which the displacements of the membranes may be measured and introduced into a central control/regulation device (computer) 20.

When in operation, the composition of the respiratory gas, such as the concentrations of oxygen, laughing gas, carbon dioxide and the like are determined continuously in a manner known in itself and also introduced into the central control/regulation device 20, which on account of the received information, regulates the supply of laughing gas, oxygen, and the like in the line system, as well as the control of the valves 16 and 18, and eventually of the valves 13 and 14 to make the patient to respire according to a certain pattern.

We claim:

1. An anesthesia respirating apparatus for patients comprising a closed line system that is provided with a first pump by means of which respiratory gas may be circulated in said closed line system and with a second pump by means of which the respiratory gas in said closed line system may be alternately compressed and decompressed to make the patient respire in accordance with a certain respiratory pattern, the closed line system being provided with means for connecting said closed line system with the patient and with further connecting means for supplying the various components of the respiratory gas to said closed line system and with still further means for withdrawing carbon dioxide that has been exhaled by the patient into the closed line system, the second pump including a plurality of simultaneously operable pump chambers connected in parallel with one another, each pump chamber having a flexible membrane which extends completely across said chamber and which separates said chamber into a primary and a secondary portion, the secondary portion of each pump chamber being connected to the closed line system and the primary portion of each pump chamber being connected to a supply of compressed air whose pressure may be varied to effect a pumping action of the membrane, and a plurality of externally controllable valves located respectively between said compressed air supply and the primary portions of said pump chambers and between the secondary portions of said pump chambers and said closed line system for selectively varying the number of said parallel pump chambers that are simultaneously operative to effect a pumping action at any given time thereby to control the pressure of the respiratory gas being circulated in said closed line system.

2. Apparatus as claimed in claim 1, wherein means are provided for determining the membrane displacement and the volume change related thereto of the secondary portion of each pump chamber.

3. Apparatus as claimed in claim 1, wherein the membrane movement towards the secondary portion of each pump chamber is limited to an end position by a stop member present in the primary portion of said pump chamber.

4. Apparatus as claimed in claim 1 wherein the rest position of the membrane is determined by a stop member present within the primary portion of each pump chamber.

5. Apparatus as claimed in claim 1 wherein means are provided for directly introducing into the closed line system and to evaporate therein a liquid anestheticum.

* * * * *